United States Patent [19]
Lopez-Claros

[11] Patent Number: 5,643,336
[45] Date of Patent: Jul. 1, 1997

[54] HEATING AND COOLING PAD

[76] Inventor: Marcelo Enrique Lopez-Claros, 871 Washington St., Raleigh, N.C. 27605

[21] Appl. No.: 370,019

[22] Filed: Jan. 9, 1995

[51] Int. Cl.⁶ ...................................................... A61F 7/00
[52] U.S. Cl. ........................ 607/104; 607/109; 607/112; 607/114; 62/530; 126/204; 165/46; 383/901
[58] Field of Search ..................... 607/104, 96, 107–112, 607/114; 62/530; 126/204; 165/46; 383/901

[56] References Cited

U.S. PATENT DOCUMENTS

| | | | |
|---|---|---|---|
| 2,323,478 | 7/1943 | Lobl | 607/96 |
| 3,804,077 | 4/1974 | Williams | 607/114 |
| 4,108,146 | 8/1978 | Golden | 607/104 |
| 4,149,541 | 4/1979 | Gammons et al. | 607/104 |
| 4,459,468 | 7/1984 | Bailey | 607/104 |
| 5,466,250 | 11/1995 | Johnson, Jr. et al. | 607/104 |

*Primary Examiner*—Robert L. Nasser
*Attorney, Agent, or Firm*—Rhodes, Coats & Bennett, L.L.P.

[57] ABSTRACT

The present invention is a heating and cooling pad for therapeutically treating the orbital, frontal, nasal, and temporal regions of a patient's head with a non-ambient temperature fluid that circulates through the pad. The pad includes a pair of molded membranes that enclose a central reservoir. Capillaries extend outwardly from opposing sides of the central reservoir into collector channels that extend around the outer periphery of the pad. The reservoir and collector channels are connected to an external source of the fluid. The design of the reservoir and capillaries is optimized to deliver the temperature-adjusting fluid to key anatomical structures. The pad includes a unique integral support structure including a universal joint, that allows adjustment of its shape.

7 Claims, 4 Drawing Sheets

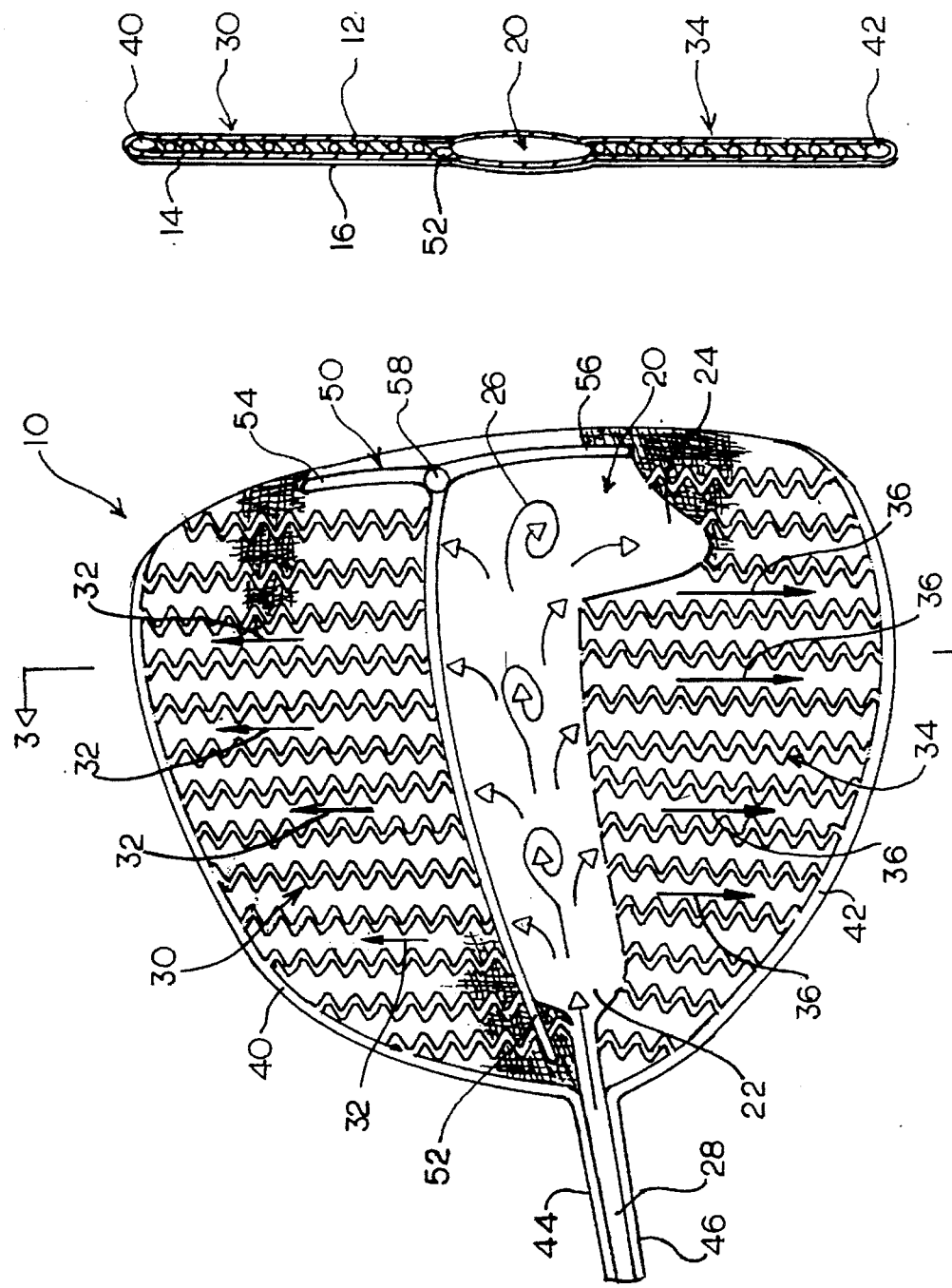

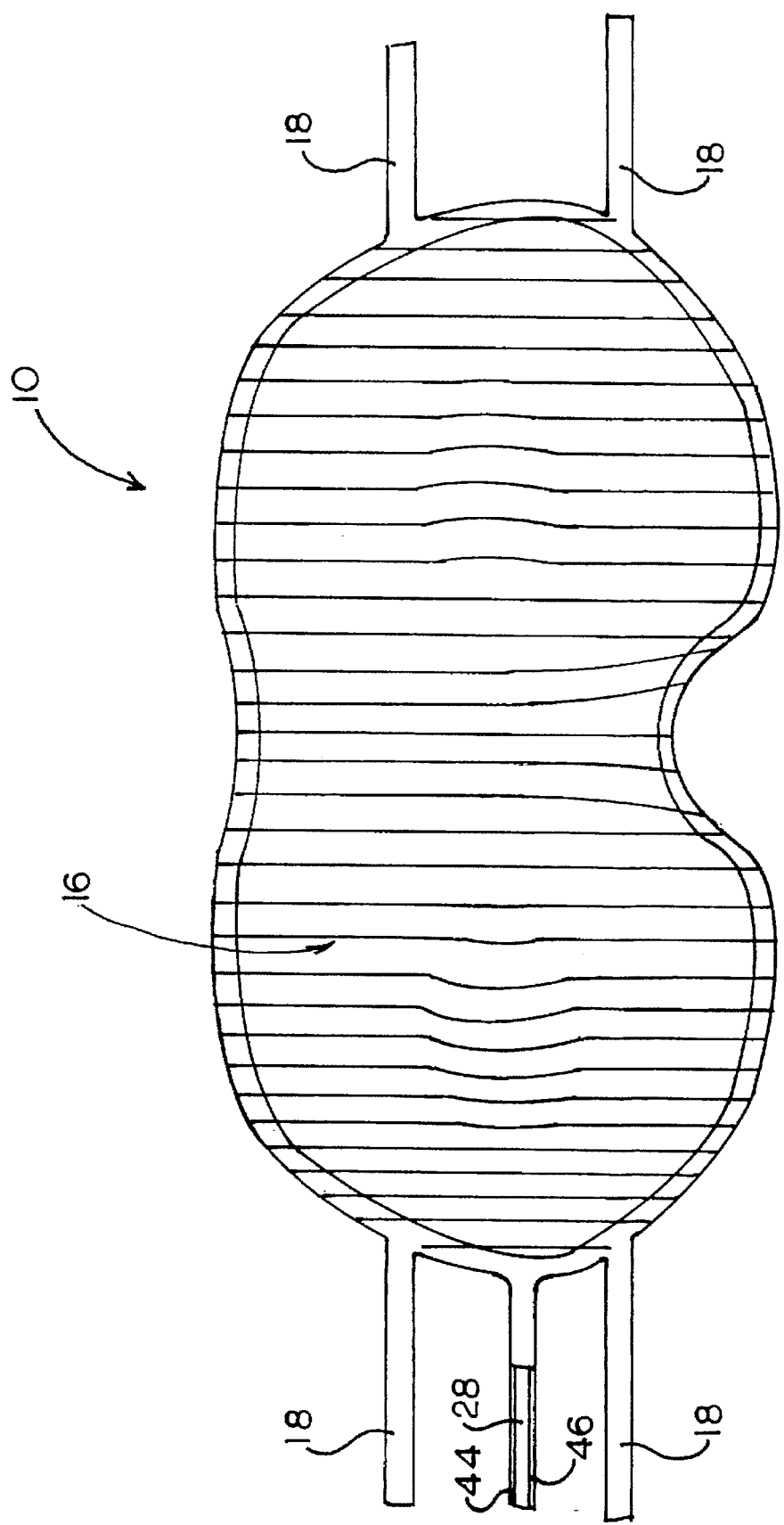

HEATING AND COOLING PAD

FIELD OF THE INVENTION

The present invention relates generally to a heating and cooling pad for treating a desired region of a patient's body with a non-ambient temperature fluid. More particularly, the present invention relates to a heating and cooling pad of the type described above, in which the pad has a three-dimensional, anatomically correct form for treating the orbital, frontal, nasal, and temporal regions of the head with a non-ambient temperature fluid.

BACKGROUND OF THE INVENTION

Heating and cooling pads are commonly used to treat a variety of bodily injuries and ailments with a non-ambient temperature fluid. For example, a cold pack is frequently used in the treatment of sprains and similar injuries to inhibit swelling in the region of the injury. Hot water bottles are also frequently used to reduce pain and promote healing.

A number of devices are known in the art for applying non-ambient temperature fluids in the treatment of injuries and other body ailments. The patents to Mason et al., U.S. Pat. No. 5,241,951; and Hardy, U.S. Pat. No. 3,674,034, disclose pads in which a non-ambient temperature fluid is circulated. The patents to Saggers, U.S. Pat. No. 4,753,242; Pagden, U.S. Pat. No. 4,781,193; Faghri, U.S. Pat. No. 5,269,369; and Gilbert, U.S. Pat. No. 3,606,890, disclose devices that use a circulating fluid for therapeutic purposes, and which conform to the patient's head. However, none of the aforementioned patents provide a pad that circulates a temperature-adjusting fluid proximate the orbital, frontal, nasal, and temporal regions of the head and, therefore, to the anatomical structures therein.

Likewise, it is known in the art to provide temperature therapy to the face with a mask that covers a person's eyes. The "EENT stay-dry ice pack" shown on page 201 of the 1993 *Baxter Medical-Surgical* catalog shows an ice pack that is worn over a person's eyes to apply cold therapy to the facial tissues. The "EENT" device holds cooling fluid in a vinyl inner bag in the manner of an ice pack shaped and worn like a mask. The "EENT" device does not provide a pad that circulates a temperature adjusting fluid through channels proximate certain specific blood vessels and structures in the orbital, frontal, nasal, and temporal regions of the head. The "EENT" device also appears to be substantially planar and does not have a molded, anatomically conforming shape. The "EENT" device also does not provide a means for regulating the temperature of the fluid contained therein.

The orbital, frontal, nasal, and temporal regions of the head are of particular interest to ophthalmologists, neurologists, ear, nose and throat specialists, internists, and psychiatrists. Heating pads may be of use to ophthalmologists to treat certain inflammations of the eye, particularly in the eyelids and lacrimal glands, which need local heat in addition to other therapeutic measures. Neurologists may use heating and cooling pads in the treatment of headaches having a vascular component. Heating and cooling pads may be of use to ear, nose, and throat specialists in the treatment of sinusitis, which is an inflammation of the sinuses. Local heat next to the sinuses improves blood circulation and the delivery of antibiotics and anti-inflammatories as well as reduces pain. Internists may use cooling pads in the management of fever, especially in circumstances where the patient cannot take anti-pyretics. Cooling pads may be the only method of controlling such fever, which if untreated could lead to febrile seizures.

The application of local heat may also be of interest to psychiatrists to provide a non-pharmacological treatment for clinical depression and other biopsychiatric disorders. It is known that abnormalities in the levels and metabolism of certain brain chemicals known as neurotransmitters can cause a host of psychiatric disorders. For example, recent research shows that 95% of the people who commit suicide have biochemical abnormalities in their brains. One neurotransmitter that has recently been the subject of extensive research is serotonin. Serotonin is intricately linked to the orbital cortex, which is the part of the brain that sits just above the eyes and affects mood and impulse control. Nerve cells manufacture, release, and absorb serotonin in quick bursts that ripple throughout the cerebrum. Low levels of serotonin are associated with clinical depression; therefore, serotonin is the target of antidepressant drugs, such as Prozac, which keep it active in the brain longer than usual. In one study of 20 suicide victims, it was shown that in almost every case, not enough serotonin had reached the orbital cortex of the brain. *Time*, Nov. 28, 1994, pp. 65–66.

The supraorbital, supratrochlear, angular, lateral nasal, external nasal, infraorbital, and ophthalmic veins all converge in the orbital cavity and eventually lead to the cavernous sinus. These vessels can be regarded and utilized as natural "heating tubes" that carry warmed blood inward proximate to the orbital cortex and the frontal cortex. The other structures of key interest are the orbital portion of the frontal bone and the frontal and ethmoid sinuses, which have blood capillaries of their own, and which are proximate to the brain.

Marcelo Enrique Lopez-Claros, M.D., postulates that increasing the blood flow to the orbital cortex will stimulate the metabolism of neurons, thereby resulting in an increased availability of serotonin. This increased level of serotonin may be achieved in at least two ways: (1) by cautious, measured increases in the temperature of the blood supply to the neurons, thereby stimulating their metabolism and increasing the natural production of serotonin; and (2) increasing the blood supply to the orbital cortex, the frontal cortex, and the temporal cortex by achieving selective vasodilatation (opening) of the vessels leading thereto, thereby delivering a larger quantity of natural chemicals such as hormones and a variety of medications with anti-depressant and antianxiety properties with known serotonergic activity to these key target areas of the brain. Additionally, with such an increase in drug availability in these areas of the brain, lower dosages and therefore lower plasma concentrations of certain drugs may be needed to achieve a therapeutic effect. The benefits of using a lower dosage of a drug include lower medication expenses and fewer side effects.

SUMMARY AND OBJECTS OF THE INVENTION

The present invention is a device for therapeutically treating the orbital, frontal, nasal, and temporal regions of a patient's head with a non-ambient temperature fluid, i.e., a cooling fluid or a heating fluid. The device comprises a pad through which the temperature-adjusting fluid is circulated. The pad comprises a pair of membranes that are molded to conform to the frontal, orbital, and temporal areas of the patient's head. The membranes enclose a central reservoir, which is connected to a source of non-ambient temperature fluid by an inlet line. A series of tortuous capillaries extend outwardly from opposing sides of the central reservoir to the outer periphery of the pad. The capillaries feed into collector channels that extend around the outer periphery of the pad.

The collector channels are connected by outlet lines to the source of the non-ambient temperature fluid to form a closed circulation system.

The design of the reservoir and capillaries is optimized to deliver the temperature-adjusting fluid proximate to key anatomical structures, including the frontal and ethmoid sinuses, orbit, eyelid, lacrimal and meibomian glands, lacrimal ducts, lacrimal sac, and naso-lacrimal duct. The temperature-adjusting fluid is also delivered proximate to facial veins in the orbital area, including the supraorbital, supratrochlear, angular, infraorbital, and external nasal, all of which converge to form the cavernous sinus, a key structure located at the base of the skull.

The main reservoir extends in a generally horizontal orientation with a vertical prolongation and lies adjacent to the orbital portion of the frontal bone and the ethmoid sinus. The capillaries extend away from the main reservoir in two directions. A first set of capillaries extends upwardly from the fluid reservoir to apply heat to the frontal bone. A second set of capillaries extends generally downwardly from the main reservoir to apply heat to the eyelid and to the facial veins as they converge and enter the orbital cavity, eventually heating the cavernous sinus. The outer membrane includes a layer of insulating material to prevent heat from escaping away from the patient's face.

In alternate forms of the invention, the heating and cooling pad could, instead of the reservoir and capillaries, include other means for adjusting the temperature of a wearer's orbital areas. These other means could include a series of capillaries without the central reservoir; a large, refillable compartment for holding a preheated or precooled fluid; a microwavable heating element or gel-pack; an endothermic or exothermic chemical reaction; an electrical resistance heating element; or any other means known to those in the art for heating or cooling parts of the body.

In a preferred embodiment of the invention, the heating and cooling pad includes an integral support structure that allows some adjustment of the shape of the pad. The integral support structure includes an orbital support that rests on the frontal bone. A frontal support and a nasal support are connected to one end of the orbital support by a universal joint to form a T-shaped support structure. The frontal support and nasal support can be adjusted to fit the pad to the contours of a particular individual's facial features.

The present invention also provides a method for treating biopsychiatric disorders by using the pad of the invention to heat the orbital and temporal areas of a person's face, thereby increasing the blood flow to the orbital cortex of the brain by increasing the temperature of blood in the cavernous sinus and the orbital cortex. The increased flow of blood results in greater neurotransmitter activity in the orbital cortex. Examples of organically based neurological disorders that may be treated using this method include: depressive disorders, anxiety disorders such as panic attacks, suicidal tendencies, obsessive/compulsive disorders, manic depression, learning disabilities, attention deficit hyperactive disorders, impulse control disorders such as kleptomania, sleep disorders, eating disorders, addictive disorders, and possibly seizure disorders. The method can also be used to treat physiological ailments such as stress, hypertension, and chronic pain.

In view of the above, it is an object of the present invention to provide a heating and cooling pad that has a three-dimensional, anatomically correct form for treating a desired region of a patient's body.

Another object of the present invention is to provide a heating and cooling pad for treating the orbital, frontal, nasal, and temporal regions of the head.

Another object of the present invention is to provide a heating and cooling pad that circulates a temperature adjusting fluid through channels proximate certain specific blood vessels and structures in the orbital, frontal, nasal, and temporal regions of the head.

Another object of the present invention is to provide a heating and cooling pad that circulates a non-ambient temperature fluid relatively slowly through a central reservoir of the pad to effectuate greater heat transfer capability in that region of the pad.

Another object of the present invention is to provide a heating and cooling pad that disposes the aforementioned central reservoir in a generally horizontal orientation adjacent to the orbital portion of the frontal bone and the ethmoid sinus.

Another object of the present invention is to provide a heating and cooling pad that includes an integral support structure that can be adjusted to fit the pad to the contours of a particular individual's facial features.

Another object of the present invention is to provide a heating pad that includes an electrical resistance heating element and the integral support structure that can be adjusted to fit the pad to the contours of a particular individual's facial features.

Another object of the present invention is to provide a method for treating biopsychiatric disorders by heating the orbital areas of a person's face to increase the temperature of blood in the cavernous sinus and in the orbital cortex of the brain.

Another object of the present invention is to provide a method for treating physiological ailments by adjusting the temperature of the orbital, frontal, nasal, and temporal regions of the head.

Other objects and advantages of the present invention will become apparent and obvious from a study of the following description and the accompanying drawings, which are merely illustrative of such invention.

BRIEF DESCRIPTION OF THE DRAWINGS

FIG. 2 is a schematic illustration of the interior of the pad showing the fluid reservoir, the capillaries, the collector channels, and the integral support structure.

FIG. 3 is a schematic cross section of the pad along lines 2—2.

FIG. 5 is depiction of a pad sized to cover both orbits.

DETAILED DESCRIPTION OF THE INVENTION

Figure 1:
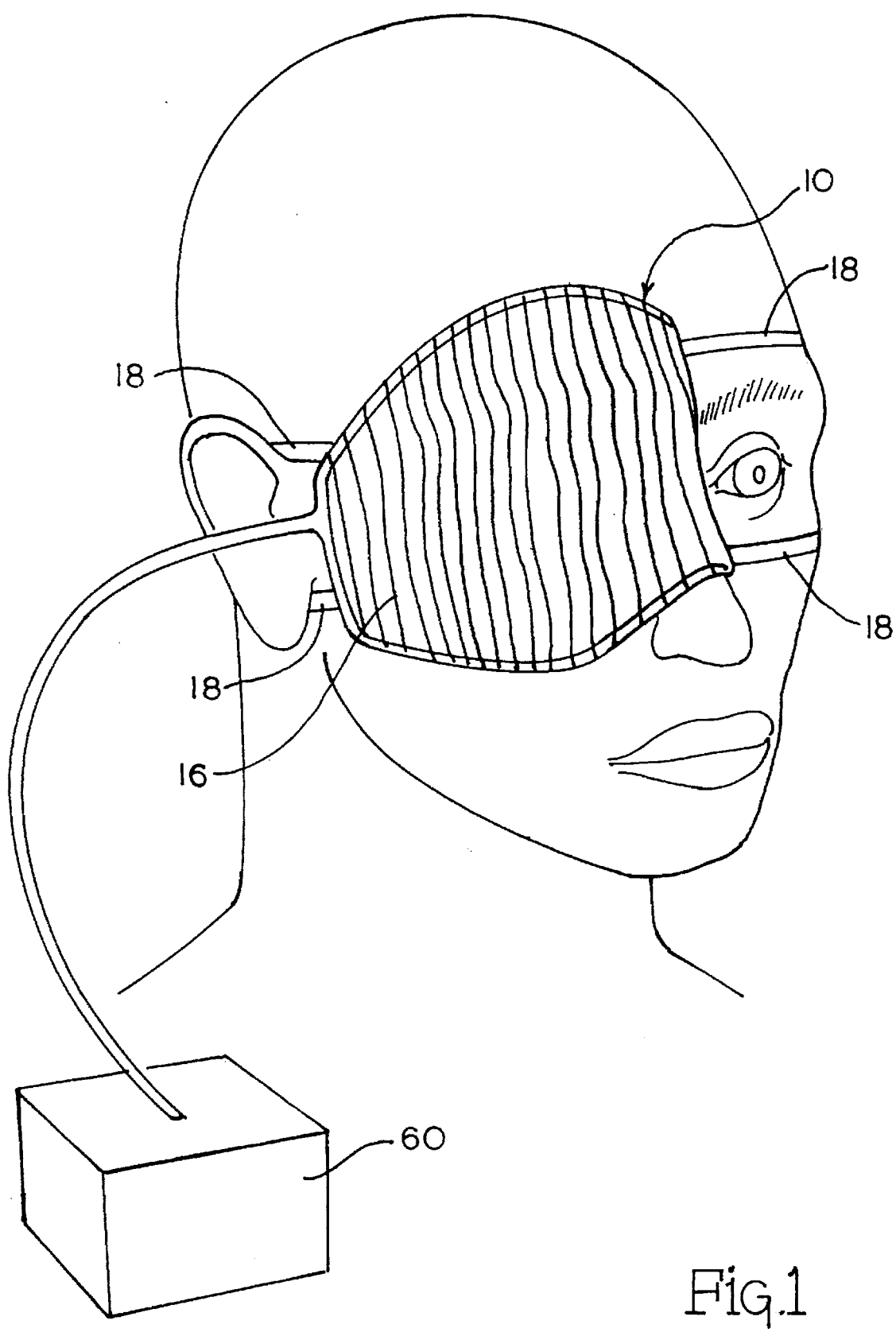
FIG. 1 is a depiction of the pad of the invention worn by a person and covering the right orbital and temporal regions of the person's head.

The present invention achieves the objects enunciated above by providing a heating and cooling pad that is anatomically molded to conform closely to the orbital area of a patient's face. Internal fluid channels are precisely positioned in the pad so that when the pad is worn, certain fluid channels, which will be described in detail below, overlie key structures of the patient's face. The pad is connected to a source of temperature-regulated fluid that circulates fluid through the channels to heat or cool these key structures as desired. Although most of the following description will describe the pad as a heating pad, this is mostly for simplicity's sake, and it should be understood that this is in no way intended to limit the application of the invention, for it is foreseen that under some circumstances it will be used as a cooling pad. It should also be understood that the pad of the invention can be sized to cover only one orbital area or can be "doubled" to cover both of a patient's orbital areas. For simplicity's sake, the following discussion will mostly address the single-sided embodiment.

Turning now to the drawings, the heating and cooling pad of the invention is described herein is generally referred to by the numeral 10. The pad 10 is generally made of an inner membrane 12 and an outer membrane 14 that are sandwiched together but that define spaces in between to form various channels, which will be described later. Both the inner membrane 12 and the outer membrane 14 are formed from a material that is pliable yet generally retains its shape upon deformation, such as a suitable plastic or other polymeric material. The membranes are, of course, waterproof and strong enough to hold up under repeated medical sterilizations. The membranes 12, 14 are not planar but are anatomically molded into a three-dimensional structure that conforms closely to the orbital areas of a person's face. It is contemplated that various sizes of pads would be manufactured to fit a variety of facial sizes and shapes. An insulation layer 16 is attached external to the outer membrane 14 to help hold in heat, and one or more adjustable support bands 18 are attached to the periphery of the pad 10 to help hold the pad 10 on a patient's head.

As mentioned above, the membranes 12, 14 define spaces therebetween. The most voluminous of these spaces is a central fluid reservoir, which is generally indicated by the numeral 20. As shown in the drawings, the majority of the reservoir 20 is its horizontal section 22, which is positioned in the pad 10 so that when the pad 10 is worn, the horizontal section 22 will overlie the orbital portion of the frontal bone and portions of the supraorbital and supratrochlear veins. The innermost end of the reservoir 20 forms a vertical prolongation 24, which overlies the ethmoid sinus and the angular vein. The reservoir 20 is connected by an inlet line 28 to a non-ambient temperature fluid source 60, which preferably acts as a pump as well as a temperature regulator. An example of such a device is the "K-MOD™ II HEAT THERAPY PUMP" shown in the 1993 *Baxter Medical-Surgical* catalog.

Communicating with and extending outwardly from the reservoir 20 are upper and lower sets of tortuous capillaries 30, 34, respectively. The capillaries 30, 34 are formed by etching numerous tortuous grooves in the inner surface of one of the membranes before the membranes are sandwiched together.

The upper capillaries 30 overlie the supraorbital areas of the frontal bone, the frontal sinus, and the portions of the supraorbital and supratrochlear veins that extend above the reservoir 20. The upper capillaries 30 feed into an upper collector channel 40, which runs along the upper periphery of the pad 10. The upper collector channel 40 is connected to the fluid source 60 by an upper outlet line 44.

The lower capillaries 34 overlie the eyelid, lacrimal and meibomian glands, lacrimal ducts, lacrimal sac, and nasolacrimal duct. The lower capillaries 34 also overlie the infraorbital, external nasal, and angular veins. The lower capillaries 34 feed into a lower collector channel 42, which runs along the lower periphery of the pad 10. The lower collector channel 40 is connected to the fluid source 60 by a lower outlet line 46.

In the preferred embodiment, a suitable non-ambient temperature fluid is circulated from the fluid source 60 to the reservoir 20 through the inlet line 28. The fluid then flows outwardly from the reservoir 20 through the upper and lower sets of capillaries 30, 34, respectively, eventually draining into the upper and lower collector channels 40, 42, respectively. The fluid then returns to the fluid source 60 through the upper and lower outlet lines 44, 46. It should be appreciated that because the reservoir 20 is the most voluminous fluid filled space in the pad 10, fluid circulates relatively slowly in the reservoir 20. This slow circulation is shown by flow lines 26. This slow circulation 26 effectuates greater heat transfer capability between the reservoir 20 and the underlying facial structures. When in the narrow, tortuous capillaries 30, 34, however, the fluid flows faster, shown by upper and lower flow lines 32, 36, respectively. This still allows heat transfer to underlying facial structures, but in a broader, more dispersed fashion.

To insure a proper, snug fit, the pad 10 of the invention not only includes anatomically molded, three-dimensional membranes, but also an integral support structure assembly, which is indicated generally by the numeral 50, disposed between the outer membrane 14 and the insulation layer 16. Because the curvature of the orbital area between the nasal arch and the deepest portion of the eye socket adjacent the corner of the eye varies from person to person, the support structure includes three adjustable members all joined together by a universal joint 58. A horizontally disposed orbital support member 52 is situated immediately above the reservoir 20 and rests on the orbital portion of the frontal bone. A frontal support member 54 is vertically situated along the inner periphery of the pad 10 above the orbital support member 52 and rests on the supraorbital portion of the frontal bone. A nasal support member 56 is vertically situated along the inner periphery of the pad 10 below the orbital support member 52 and rests on the nasal bone. The frontal support 54 and the nasal support 56 are both joined to the orbital support 52 in a T-shape by the universal joint 58, which is located at the innermost end of the orbital support 52.

Figure 4:
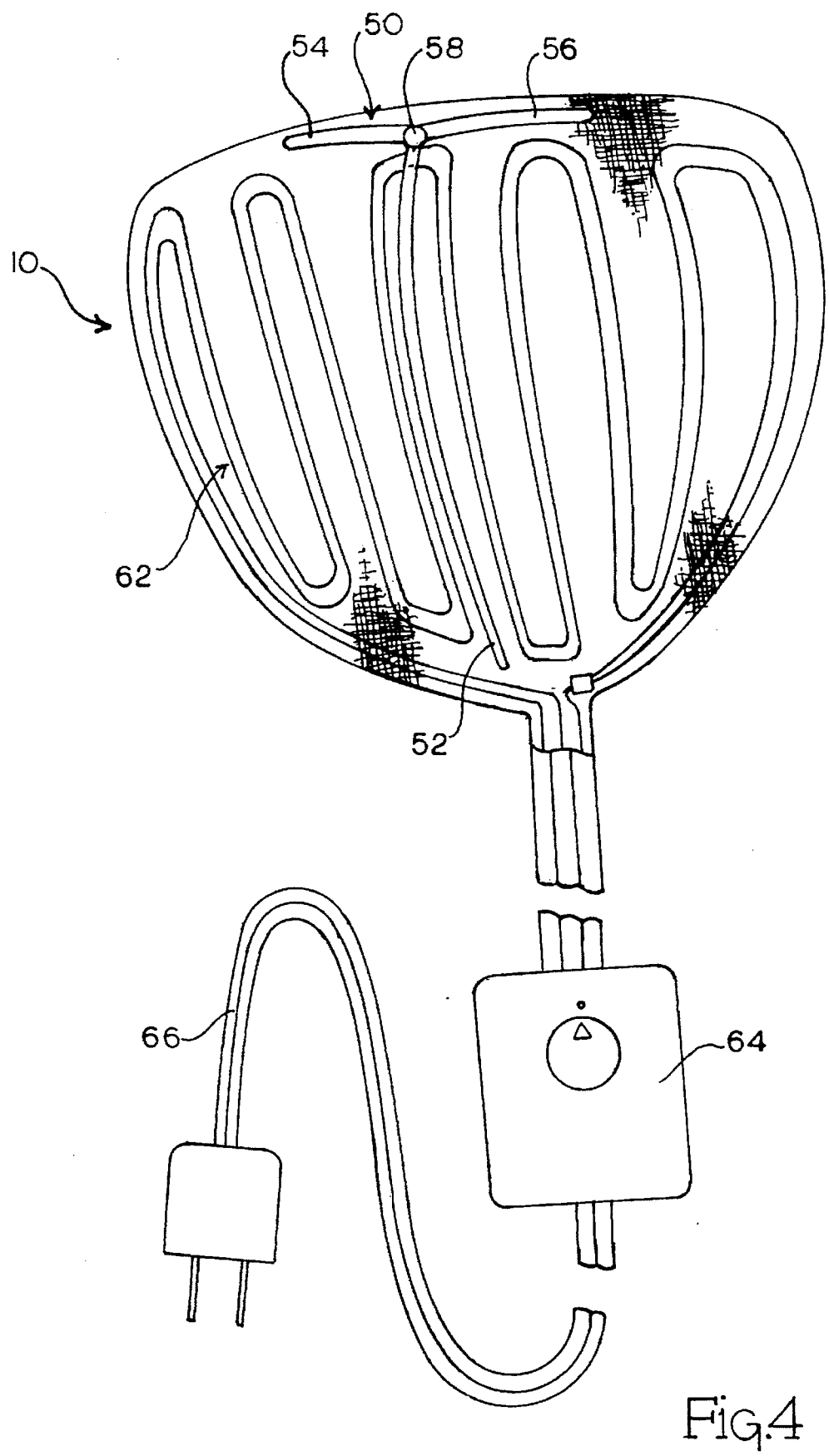
FIG. 4 is a depiction of an alternate embodiment of the pad having an electrical resistance heating element.

An alternate embodiment of the present invention is shown in FIG. 4, which illustrates the heating pad 10 having a conventional electrical resistance heating element 62 enclosed within the pad 10, a conventional electric thermostat heat controller 64, and a power cord 66. However, the electric embodiment of the heating pad 10 differs from conventional electric heating pads because the electric heating pad of the invention is formed with the anatomically conforming shape described above. The electric heating pad 10 preferably also includes the support structure assembly 50 described above, including the orbital support 52, frontal support 54, and nasal support 56, all joined together by the U-joint 58.

It should be appreciated that in other alternate embodiments of the present invention, the integral support structure assembly 50 could also be incorporated into other conventional heating and cooling pads. For example, the support structure 50 could be included in a self-contained pad in which two membranes define one or more fluid compartments for containing a non-circulating, temperature-adjusting fluid. This could be achieved by incorporating the integral support structure assembly 50 into, for example, a microwavable heating pad or a refrigerable cooling pad that is anatomically molded to fit over the orbit. The support structure could also be incorporated into a pad in which two chemicals are mixed to produce an endothermic or exothermic reaction to therefore cool or heat, respectively, the orbital areas of a person's face.

The present invention provides a method for treating biopsychiatric and physiological disorders by using the pad 10 to heat the orbital and temporal areas of a person's face, thereby increasing the temperature of blood in the cavernous sinus and in the orbital cortex of the brain. By heating the orbital and temporal areas of the face with the pad 10 of the invention, the supraorbital, supratrochlear, angular, lateral nasal, external nasal, infraorbital, and ophthalmic veins, the cavernous sinus, the orbital portion of the frontal bone, and the frontal and ethmoid sinuses all become natural heat conductors that carry warmed blood inward proximate to the orbital cortex and the frontal cortex of the brain. This increase in blood temperature results in an increase in blood flow to the orbital cortex and the frontal cortex.

This increase in blood flow to the orbital cortex stimulates the metabolism of neurons, thereby resulting in increased neurotransmitter activity, including serotonergic activity. This increased activity of serotonin is achieved in at least two ways. First, increases in the temperature of the blood supply to the neurons stimulates their metabolism and increases the natural production of serotonin. Second, increases in the blood supply to the orbital cortex, the frontal cortex, and the temporal cortex, by achieving selective vasodilatation of the vessels leading thereto, results in the delivery of: (1) a larger quantity of natural chemicals such as hormones, and (2) a variety of medications with antidepressant and antianxiety properties with known serotonergic activity, to these key target areas of the brain. Additionally, with such an increase in drug availability in these areas of the brain, lower dosages and therefore lower plasma concentrations of certain drugs are needed to achieve a desired therapeutic effect.

Examples of organically based neurological disorders (biopsychiatric disorders) that may be treated using the method of the invention include: clinical depression, anxiety and stress disorders such as panic attacks, suicidal tendencies, obsessive/compulsive disorders, learning disabilities, attention deficit hyperactive disorder, impulse control disorders such as kleptomania, sleep disorders, eating disorders, addictive disorders, psychosis, learning disabilities, manic-depressive disorders, and possibly seizure disorders. Examples of physiological ailments that may be treated using the method of the invention include stress, hypertension, headaches with a vascular component, and chronic pain.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An anatomically conforming pad for adjusting the temperature of blood in the orbital area of a person's face, comprising:

(a) a pair of pliable membranes;

(b) temperature adjusting means, disposed between the pliable membranes, for adjusting the temperature of blood in the orbital area of a person's face;

(c) said pliable membranes being three-dimensionally, anatomically molded to fit the contours of the orbital area of the face so as to optimize heat transfer between the pad and the orbital area of the face;

(d) said pliable membranes being constructed of a material that generally retains its shape upon deformation; and (e) a plurality of adjustable support members for shaping the pad to fit the contours of varying facial features, said adjustable support members all joined together by a universal joint.

2. The pad of claim 1 wherein said plurality of adjustable support members include an orbital support member that is adapted to rest on the orbital portion of the frontal bone, a frontal support member that is adapted to rest on the supraorbital portion of the frontal bone, and a nasal support member that is adapted to rest on the nasal bone.

3. The pad of claim 2 wherein the orbital support member, the frontal support member, and the nasal support member are all joined together in a T-shape by the universal joint.

4. The pad of claim 1 wherein the temperature adjusting means comprises a plurality of channels containing a non-ambient temperature fluid.

5. The pad of claim 1 wherein the temperature adjusting means comprises an electrical resistance heating element.

6. The pad of claim 1 wherein the pad is sized to fit over one orbit.

7. The pad of claim 1 wherein the pad is sized to fit over both orbits.

* * * * *